United States Patent [19]

Haerr

[11] 4,034,759
[45] July 12, 1977

[54] MOISTURE-EXPANDABLE PROSTHESIS

[75] Inventor: Raymond H. Haerr, Cincinnati, Ohio

[73] Assignee: Xomed, Inc., Cincinnati, Ohio

[21] Appl. No.: 608,148

[22] Filed: Aug. 27, 1975

[51] Int. Cl.$^2$ .................... A61F 1/18; A61M 31/00
[52] U.S. Cl. ................................ 128/260; 128/151
[58] Field of Search .......... 128/151, 152, 260, 263, 128/269, 270, 296, 285, 341

[56] References Cited

U.S. PATENT DOCUMENTS

| 1,438,064 | 12/1922 | Simmons | 128/260 |
|---|---|---|---|
| 2,427,664 | 9/1947 | Dunbar et al. | 128/152 |
| 3,068,867 | 12/1962 | Bletzinger et al. | 128/285 |
| 3,347,237 | 10/1967 | Jones | 128/285 |
| 3,805,785 | 4/1974 | Marginet | 128/263 |
| 3,900,030 | 8/1975 | Bashan | 128/285 |
| 3,903,232 | 9/1975 | Wood et al. | 128/285 |

FOREIGN PATENT DOCUMENTS 733,542  7/1955  United Kingdom ............... 128/152

Primary Examiner—Robert W. Michell
Assistant Examiner—Henry J. Recla
Attorney, Agent, or Firm—J. Warren Kinney, Jr.

[57] ABSTRACT

A hollow-cylindrical tube of dehydrated, regenerated cellulose sponge material is tightly compressed to provide an elongate member of minimal diameter having sufficient rigidity to be inserted endwise into a body opening where it will, when moistened, expand radially whereby to substantially engage the inner peripheral walls of the opening for securing it against accidental or unintentional dislodgement therefrom. When used in association with an ear canal an axial opening through the expanded member permits sound waves to reach the ear drum. The device can be used to apply medicament by expanding the compressed tube with a liquid medicament.

9 Claims, 6 Drawing Figures

MOISTURE-EXPANDABLE PROSTHESIS

BACKGROUND OF THE INVENTION

1. Field of the Invention

The invention relates to a dehydrated wick of cellular material which, when hydrated, will rapidly expand radially in an effort to assume its dimensions, prior to compression. The dehydrated wick possesses sufficient rigidity to enable it to be inserted endwise into various body cavities and openings, and when so positioned and hydrated it will rapidly expand whereby to snugly engage the inner peripheral walls of the opening for thereby providing an ideal media for the application of medicament to the walls of the body opening.

2. Description of the Prior Art

The Stephan U.S. Pat. No. 1,210,720, dated Jan. 2, 1917, discloses a surgical cotton splint fabricated into a substantially projectile-shaped member by feeding one or more laminae of absorbent cotton to a rewind spindle and placing the cotton toward the axis or along the spindle and beyond the point thereof as the cotton winds upon itself. Each of the cotton layers become so immeshed with the adjacent layer that there is no possibility of the finished product unwinding. By reason of the thinness of the successive layers, the resulting product is a homogenous body of compacted cotton fiber arranged about a center in an elongated pointed form and having sufficient stiffness to be utilized without a handle for use by surgeons, oculists, and nurses for the cleaning of nostrils, ears, etc. The aforesaid splint is not adapted to expand or swell when subjected to moisture.

Applicant is also aware of the following U.S. patents:

Strauss U.S. Pat. No. 2,490,168 which discloses a sinus medication applicator which comprises an elongate, hollow stem having a plurality of lateral openings in open communication with a porous or spongy body member secured to and carried by the stem;

Pietro U.S. Pat. No. 3,506,009, which is directed to a method of making styptic-tipped medical sticks;

Brillant U.S. Pat. No. 3,018,778, which discloses a pellet fabricated from material which expands when it is wet and becomes soft so as to yield and become distorted under light pressure, either to fill or to reach all surfaces of a cavity, or to provide a larger wiping surface and to provide more intimate contact with the surface to be dried or treated, wherein the pellet is fabricated from "sponge rubber", and wherein the pellet is secured to and carried by a thin, flexible applicator of wood, metal or plastic;

Strauss U.S. Pat. No. 2,710,222, which discloses a sponge applicator which is secured to and carried by a hollow tube through which medicament, and other liquids, is supplied to the interior of the sponge;

Davis U.S. Pat. No. 2,510,961, which discloses an ear cleaner which includes a pad of soft, elastic, porous material having good cleansing and scrubbing qualities such as sponge or foam rubber;

Negri U.S. Pat. No. 2,642,065, which discloses a vial containing an analgesic fluid in a protecting container having a substantially fresto-conical shape, from one end of which an absorbent element projects for the purpose of spreading fluid inside of the auditory meatus;

Hartop U.S. Pat. No. 3,865,108, discloses a drug delivery device having a drug containing zone associated with and partially defined by a material which swells on contact with body fluids. When swelling occurs, the pressure on the drug containing zone expells the drug from the device.

DESCRIPTION OF THE PREFERRED EMBODIMENTS

Figure 1:
FIG. 1 is a perspective view of a wick of the present invention in a fully compressed condition.
Figure 3:
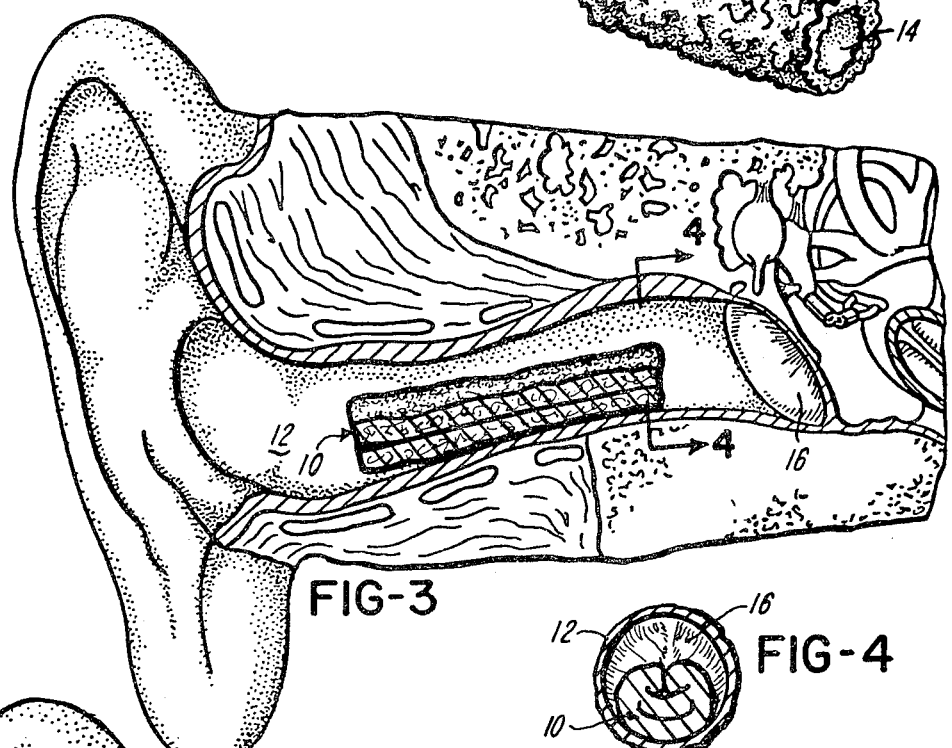
FIG. 3 is a sectional view illustrating the wick of FIG. 1 inserted into the ear canal of a patient.
Figure 4:
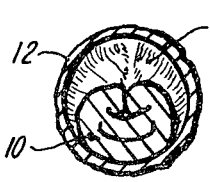
FIG. 4 is a view taken on line 4—4 of FIG. 3.

With particular reference to FIGS. 1, 3, and 4, the numeral 10 denotes, generally, an elongate, substantially cylindrical wick of compressed, dehydrated, cellular material which is sufficiently rigid to be inserted, endwise, into a body opening, such as, by way of example, an ear canal 12, or the like.

Figure 2:
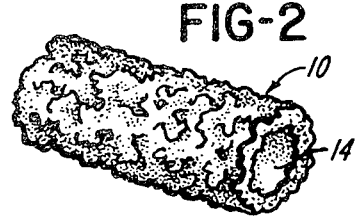
FIG. 2 is a perspective view illustrating the wick of FIG. 1 in a fully expanded condition.
Figure 5:
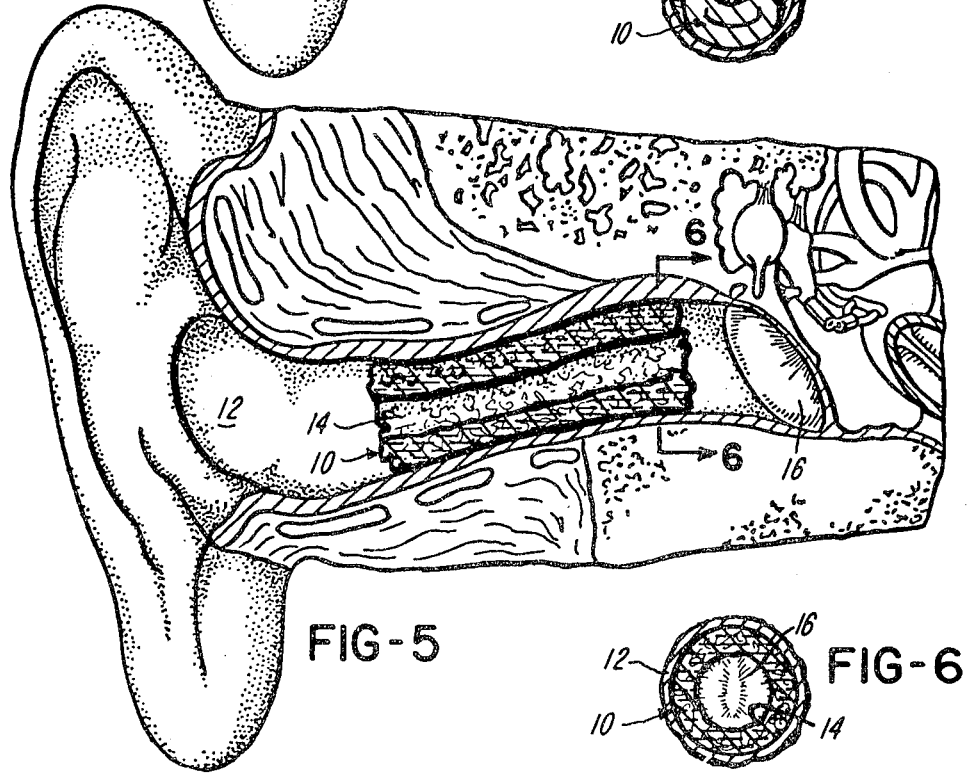
FIG. 5 is a view similar to FIG. 3 showing the wick in a fully expanded condition.
Figure 6:
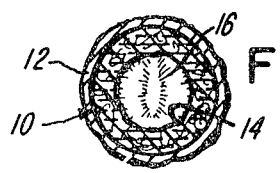
FIG. 6 is a view taken on line 6—6 of FIG. 5.

The physical characteristics of the wick are such that when hydrated it will expand radially into an elongate, hollow, substantially cylindrical shape, as illustrated in FIGS. 2, 5 and 6.

In those instances in which the dehydrated wick has been inserted into an ear canal 12, the outer surface thereof, will, when the wick has been hydrated, expand radially outwardly whereby to substantially fill and engage the interior surface of the ear canal for thereby precluding its accidental or unintentional dislodgement therefrom.

When utilized, as illustrated in FIGS. 3 and 5, the wick is ideally suited for retaining a medicant in intimate contact with an adjacent surface of the ear canal, and since the member, when expanded is hollow, having an axial opening 14 therethrough, the presence of the wick within the ear canal permits the passage of sound waves to the tympanic membrane 16, whereby the presence of the wick will induce but a minimal hearing impairment to the patient.

Uniformly satisfactory results have been obtained in those instances in which the cellular material comprises fine pore regenerated cellulose sponge as manufactured by the O-Cell-O Division of General Mills, Inc. from sulphite wood pulp.

When the subject members are utilized as an ear wick, as illustrated in FIGS. 1 and 2, the length thereof may approximate ¾ inch with an outside diameter of ⅜ inch and an inside diameter of from ⅛ inch to ¼ inch.

The compressed, dehydrated, substantially cylindrical, elongate wick of FIGS. 1, 3, and 4 is fabricated from a dehydrated, cylindrical, elongate, hollow member as illustrated in FIG. 2, such as, by way of example, by the application of a radial, rolling, compressive force to the outer surface of the hollow cylinder of FIG. 2 whereby its outer diameter will be radially compressed to about ⅛ inch — while retaining its overall length of ¾ inch. During compression the axial opening 14 is completely closed.

The thus compressed, dehydrated, elongate, substantially cylindrical wick is sufficiently rigid to permit it to not only be handled, but to be inserted endwise into a body opening, such as, by way of example, an ear canal. After the wick has thus been positioned it will, when subjected to moisture, such as, by way of example, by the application of a liquid medicament, rapidly expand radially whereby to seek to resume the dimensions, of FIG. 2, which it had before it was compressed to the wick of FIG. 1.

It should, of course, be understood that the fully expanded dimensions of the wick of FIG. 2 will, for any particular application, be determined by the dimensions of the body opening into which the wick is to be inserted. After the fully expanded dimensions have been determined, the fully compressed dimensions of the wick are a function of the wall thickness of the fully expanded cylinder and the degree of compression to which the dehydrated cylinder of FIG. 2 is subjected.

Uniformly satisfactory results have been obtained in those instances in which the outside diameter of the expanded, dehydrated, cellulose sponge material of FIG. 2 approximates 9 mm, and wherein the outside diameter after compression approximates 2 mm. In other words, the diameter after compression is about 20 percent of the original non-compressed diameter of FIG. 2. In other instances the degree of reduction in diameter may vary from 30 percent to 80 percent.

An object of the compression is to so reduce the outside diameter of the elongate wick or prosthesis such that it may be inserted endwise into a body opening, such as, by way of example, an ear canal 12 without contacting the inner surface of the opening during insertion, in order to eliminate or at least substantially reduce, contact during insertion and thereby minimize the pain which would result by reason of the insertion of an expanded wick member into an inflamed passage of a body opening. Once in place, the radial expansion which occurs in the prosthesis incident to the application of moisture, causes the prosthesis to rapidly, but gently, expand radially to provide contact between its outer surface and the inner surface of the ear canal.

The expansion of a prosthesis, in situ, may be effected by the application of a liquid medicament to the prosthesis of FIG. 3, in which event the medicant, per se, will provide the necessary moisture to produce the desired expansion or, the prosthesis of FIG. 3 may be subjected to moisture, such as sterile water for effecting expansion, as illustrated in FIG. 5, after which medicament may be applied to the fully expanded prosthesis. It will be understood that medicament applied to the prosthesis will be disposed in prolonged contact with the adjacent surfaces of the ear canal, thereby providing a beneficial and prolonged application of medicament to inflamed portions of the ear canal.

It should also be understood that if desired, the outer surface of the compressed prosthesis of FIG. 1 may be suitably coated with a paste-like substance, such as salve, ointment, or cream.

While the prosthesis has been described in association with an ear canal, it should be understood that it may be utilized with any body opening.

After the prosthesis or wick has been fully compressed, as in FIG. 1, it should be suitably stored in a substantially moisture free environment until such time as it is to be used.

What is claimed is:

1. An elongate, compressed, collapsed, tubular, hollow, moisture-expandable ear canal prosthesis for applying medicament to an interior surface of an ear canal comprising a radially compressed, hollow cylinder of expanded, dehydrated, cellulose, sponge-like material wherein the outside diameter of said compressed, collapsed prosthesis approximates 2 mm, said material when hydrated by a medicament expands radially to the dimensions of the hollow cylinder prior to compression, whereby said prosthesis applies medicament to the interior surfaces of the ear canal when expanded, and is characterized by an open, axial passage therethrough.

2. A prosthesis as called for in claim 1, which is sufficiently rigid for endwise insertion into a body opening without distortion or bending.

3. A prosthesis as called for in claim 1, wherein the cellulose sponge material is characterized by a multiplicity of fine pores.

4. A prosthesis as called for in claim 1, which, when hydrated, expands to its original pre-compressed dimensions.

5. The method of applying medicament over a prolonged period of time to the inner surface of an ear canal, which comprises the steps of inserting an elongate, compressed, collapsed, hollow, cylindrical member of dehydrated, cellular, sponge-like material into the ear canal, wherein the outer diameter of said collapsed, cylindrical member is less than the inside diameter of the ear canal, and of then hydrating said member in situ with a liquid medicament to cause it to expand radially outward to dispose its outer surface in contacting relationship with adjacent portions of the inner surface of the ear canal and thereby apply the medicament thereto, said member, when expanded, providing an open passageway through said member for the passage of sound waves to the tympanic membrane of the ear.

6. A method of applying a medicament to an interior surface of an ear canal over a prolonged period of time comprising the steps of:
    inserting a compressed, collapsed, cylindrical member of dehydrated, cellular, sponge-like material having a collapsed, axial passage completely through said member into the ear canal, said inserting occurring with only a small amount of contact between said member and the interior surface of the ear canal, for locating said collapsed member entirely within the ear canal;
    hydrating said member in situ with a liquid medicament to cause it to expand radially outward into substantial contact with the interior surface of the ear canal and thereby apply the medicament thereto and provide an axial, open, obstruction-free passageway through said expanded member for the passage of sound waves to the tympanic membrane of the ear while said member is in place within the ear canal.

7. The method of claim 6, wherein said member expands from a diameter of about 2 mm to 9 mm.

8. The method of claim 6, which includes an initial step of storing said compressed collapsed cylindrical member in a moisture-free environment prior to inserting same into an ear canal.

9. The method of claim 6, wherein said member is inserted into the ear canal without distorting said member.

* * * * *